Figure 1:
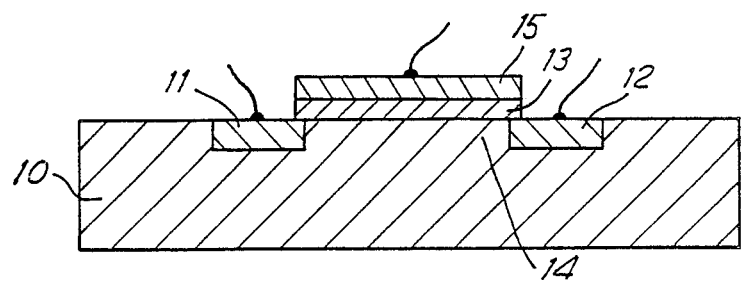

United States Patent [19]
Sibbald et al.

[11] Patent Number: 4,931,851
[45] Date of Patent: Jun. 5, 1990

[54] GAS SENSITIVE DEVICE

[75] Inventors: Alastair Sibbald, Maidenhead; Brian C. Webb, Sunbury; Ian Robins; John F. Ross, both of Hayes; Edward C. Bell, Windsor, all of Great Britain

[73] Assignee: Thorn EMI plc, London, England

[21] Appl. No.: 25,049

[22] Filed: Mar. 12, 1987

[30] Foreign Application Priority Data

Mar. 12, 1986 [GB] United Kingdom ................ 8606045

[51] Int. Cl.$^5$ ...................... H01L 29/66; H01L 29/96
[52] U.S. Cl. ..................................... 357/25; 73/31.06; 350/96.29; 357/23.1
[58] Field of Search ................................ 357/25, 23.1; 350/96.29; 73/26

[56] References Cited

U.S. PATENT DOCUMENTS

| | | | |
|---|---|---|---|
| 4,127,462 | 11/1978 | Blurton et al. | 204/195 R |
| 4,242,302 | 12/1980 | Kitamura et al. | 422/94 |
| 4,290,586 | 9/1981 | Kane et al. | 73/23 X |
| 4,313,338 | 2/1982 | Abe et al. | 73/23 |
| 4,316,140 | 2/1982 | Senturia | 357/25 X |
| 4,347,732 | 9/1982 | Leary | 73/23 |
| 4,601,914 | 7/1986 | Barnes et al. | 427/421 X |

FOREIGN PATENT DOCUMENTS

| | | |
|---|---|---|
| 0102067 | 3/1984 | European Pat. Off. . |
| 2368802 | 5/1978 | France . |
| 55-160841 | 12/1980 | Japan ..................................... 357/25 |
| 1280809 | 7/1972 | United Kingdom . |
| 1285731 | 8/1972 | United Kingdom . |
| 1374575 | 11/1974 | United Kingdom . |
| 1433071 | 4/1976 | United Kingdom . |
| 1477082 | 6/1977 | United Kingdom . |
| 2072418 | 9/1981 | United Kingdom . |
| 2096824 | 10/1982 | United Kingdom . |
| 2101806 | 1/1983 | United Kingdom . |
| 2160356 | 12/1985 | United Kingdom . |

OTHER PUBLICATIONS

Bergveld, P. "The Impact of MOSFET-Based Sensors", Sensors and Actuators, 8 (1985) 109–127.
"A Hydrogen Sensitive MOS Field Effect Transistor", by I. Lundstrom, vol. 26, Applied Physics Letters 55–57 (1975).
Performance of Carbon Monoxide-Sensitive MOSFET's with Metal-Oxide Semiconductor Gates, Dobos et al., IEEE Trans. on Electron Devices, ED-32, No. 7, pp. 1165–1169, Jul. 1985.
Ion-Sensitive Field-Effect Transistors with Inorganic Gate Oxide for pH Sensing, Akiyama et al., IEEE Trans. on Electron Devices, vol. II, ED-29, No. 12, pp. 1936–1941, Dec. 1982.

Primary Examiner—Edward J. Wojciechowicz
Attorney, Agent, or Firm—Fleit, Jacobson, Cohn, Price, Holman & Stern

[57] ABSTRACT

A gas sensitive device, for example a gas sensitive MISFET (FIGS. 1 to 3) has a gas-sensitive electrode (15) comprising a catalytically active metal (e.g. Pt or Pd) and a non-metallic material (e.g. $SiO_2$) mixed with, or deposited at an exposed surface of, the metal to modify the catalytic activity of the metal. The electrode has an enhanced sensitivity to, and selectivity of, certain gases. The composite material is applicable to other gas-sensitive devices, e.g. an optical fibre gas sensor.

11 Claims, 4 Drawing Sheets

GAS SENSITIVE DEVICE

This invention relates to a gas sensitive device and it relates particularly, though not exclusively, to a gas sensitive metal-insulator-semiconductor (MIS) device, for example, a MIS field effect transistor (MISFET).

A known gas sensitive MISFET, described by I Lundstrom in "A Hydrogen Sensitive MOS Field Effect Transistor", Vol. 26 Applied Physics Letters 55–57 (1975), has a catalytically active gate electrode in the form of a thin film of platinum or palladium. Molecular hydrogen dissociates at the electrode surface and the hydrogen atoms produced diffuse through the film and are adsorbed at the gate electrode/gate insulator interface. The dipole moments of the adsorbed atoms produce a detectable change in the threshold voltage of the device and so give an indication of the concentration of hydrogen gas to which the device is exposed. If a thin, porous film is used, so that the gate insulator is partially exposed to a target gas, the device becomes sensitive to ammonia gas also. However, the gate electrode then tends to have poor electrical conductivity, and in some applications this may be unsatisfactory. Furthermore the device may be subject to interference from other, unwanted gases which may penetrate the film and become absorbed in the gate insulator. Also, a thin porous film, having the required physical characteristics, can prove difficult to manufacture with reliability.

It is one object of the present invention, therefore, to provide a gas sensitive device which at least alleviates some, or all, of the above-described problems.

Accordingly there is provided a gas sensitive device wherein a gas-sensitive element comprises a catalytically active metal and a non-metallic material mixed with, or deposited at an exposed surface of, the metal to modify the catalytic activity of the metal, the non-metallic material being an oxide of a metal, an oxide of a semiconductor, a metal zeolite or a mixture of more than one of said non-metallic materials.

The inventors have discovered that a gas-sensitive element having a composite structure, as defined, may have an enhanced catalytic activity with respect to one, or a range of different, hydrogen-containing gases, giving the associated device a greater sensitivity. The inventors also find that the form of the element can also influence the selectivity of the device.

The inventors also envisage that with an appropriate choice of constituent materials it is possible to suppress the catalytic activity of the element with respect to one or more selected gases, thereby enhancing selectivity of the device.

In an embodiment the element comprises a first layer of a first catalytically active metal bearing a second layer of a second catalytically active metal mixed with said non-metallic material. The first and second catalytically active metals may be the same.

Catalytically active metals used may be selected from the transition metals, or alloys thereof, and said non-metallic material may comprise a selected one of, or a mixture formed from two or more of, the group consisting of silicon dioxide, aluminium oxide, titanium dioxide, cerium dioxide, magnesium oxide, vanadium pentoxide and metal zeolites.

In one application of the invention the gas-sensitive element comprises a gas-sensitive electrode and in an example the gas-sensitive device may be a gas-sensitive metal-oxide-semiconductor field effect transistor (MISFET) wherein the gas-sensitive electrode is the gate electrode.

In an especially useful example the inventors find that a MISFET has a surprisingly enhanced sensitivity to ammonia gas and to methane if the gate electrode consists of, or includes, a cermet of platinum and silicon dioxide.

In another application of the invention the gas sensitive device comprises an optical fibre gas sensor, and said gas-sensitive element comprises an optical fibre bearing a coating formed from said catalytically active metal and said non-metallic material.

Figure 2:
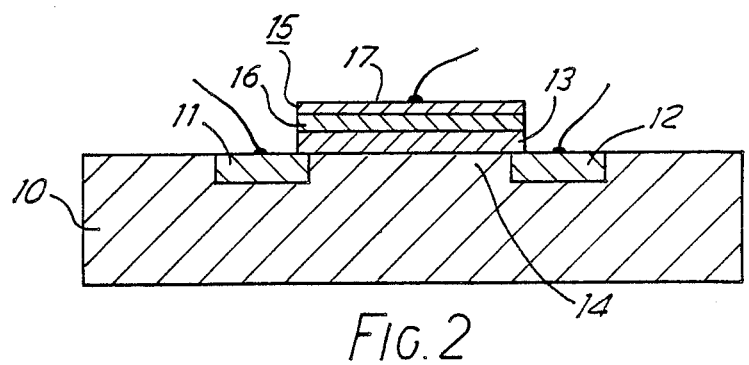
Figure 3:
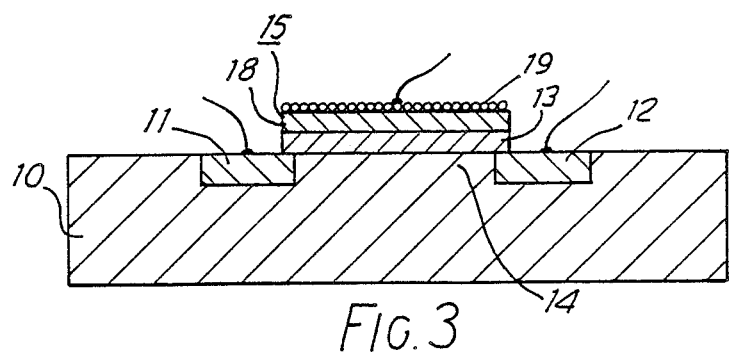

In order that the inventor may be carried readily into effect, embodiments thereof are now described, by way of example only, by reference to the accompanying drawings of which, FIGS. 1 to 3 show cross-sectional views through a MIS field effect transistor having different gate electrode structures and FIGS. 4 to 8 show the responses of different MISFETs to methane, hydrogen and ammonia gas.

The invention will be described initially by reference to a device having a gas sensitive electrode, and although a gas-sensitive MISFET is described, by way of example, it will be understood that the invention also encompasses other electrical devices including a gas-sensitive electrode, for example other varieties of FET structures other than the planar example described herein, MIS capacitors, Schottky barrier devices, electrochemical cells, surface acoustic wave devices, piezoelectric crystal oscillators and chemoresistive devices.

Referring now to FIG. 1 of the drawings, a gas sensitive MISFET comprises a substrate 10, formed of a semiconductor material of one conductivity type (p-type, say), and drain and source regions 11,12 of the opposite conductivity type (n-type say) formed in a surface of the substrate. A gate insulator layer 13, typically of silicon dioxide or silicon dioxide/silicon nitride, is deposited on the substrate between the drain and source regions so as to overlie the drain-source channel 14, and a catalytically active gate electrode 15 is deposited on the gate insulator layer.

In contrast to a MISFET of the kind described by Lundstrom, wherein the gate electrode comprises a thin film of pure platinum or palladium, a MISFET in accordance with the present invention has a composite gate electrode.

In one example of the invention, electrode 15 comprises an intimate mixture of platinum (or palladium) and silicon dioxide deposited on the gate insulator by co-sputtering the constituents. This may be achieved either by sputtering the platinum (or palladium) and silicon dioxide simultaneously, or alternatively by presenting these materials to the sputtering beam alternately, for short, predetermined periods. The inventors have found that a composite electrode of this kind has an enhanced catalytic activity with respect to certain reducing gases, especially ammonia and methane. Moreover, a relatively thick (eg 20–100 nm) electrode can be used giving an electrical conductivity which proves to be adequate for many applications. If a greater electrical conductivity is needed, a composite electrode of the form shown in FIG. 2 may prove useful. In this case, the electrode comprises a layer 16 of pure metal (eg Pt or Pd) provided with a relatively thin (eg 1–10 nm) coating 17 of the platinum (or palladium)-/silicon dioxide mixture. This structure is particularly effective if layer 16 is non-porous and the target gas interacts with a surface region only of the electrode.

In a yet further embodiment of the invention, shown in FIG. 3, the gate electrode comprises a non-porous layer 18 of pure metal (eg Pt or Pd), typically 10–100 nm thick, provided with a thin (eg 0.1–10 nm) porous coating 19 of silicon dioxide which partially exposes layer 18 to a target gas. If desired coating 19 could be suitably patterned to create discrete islets on layer 18. Again this form of composite electrode exhibits an enhanced catalytic activity and has a relatively high electrical conductivity.

In comparison with a gate electrode of the kind described by Lundstrom, a composite gate electrode, as used in a MISFET according to the present invention, may be relatively thick thereby presenting an effective barrier layer between the atmosphere and the gate insulator, especially if part of the electrode is non-porous. This tends to reduce interference from other, unwanted gases.

The inventors have discovered that a composite electrode in accordance with the present invention has enhanced catalytic activity with respect to certain reducing gases, including ammonia, hydrogen, methane, carbon monoxide, hydrogen sulphide, and hydrocarbons such as the alkanes and alkenes.

Figure 4:
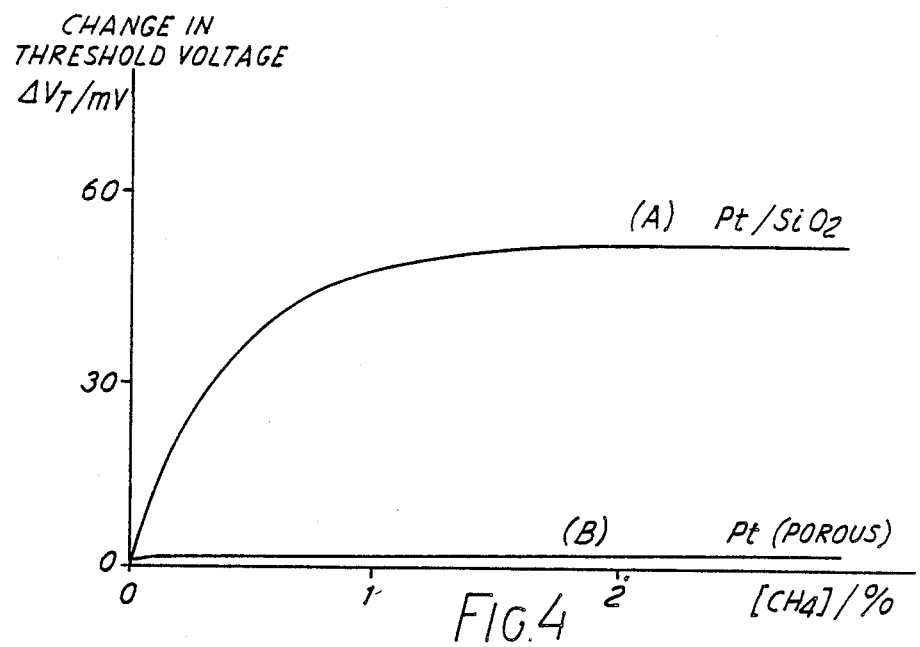
Figure 5:
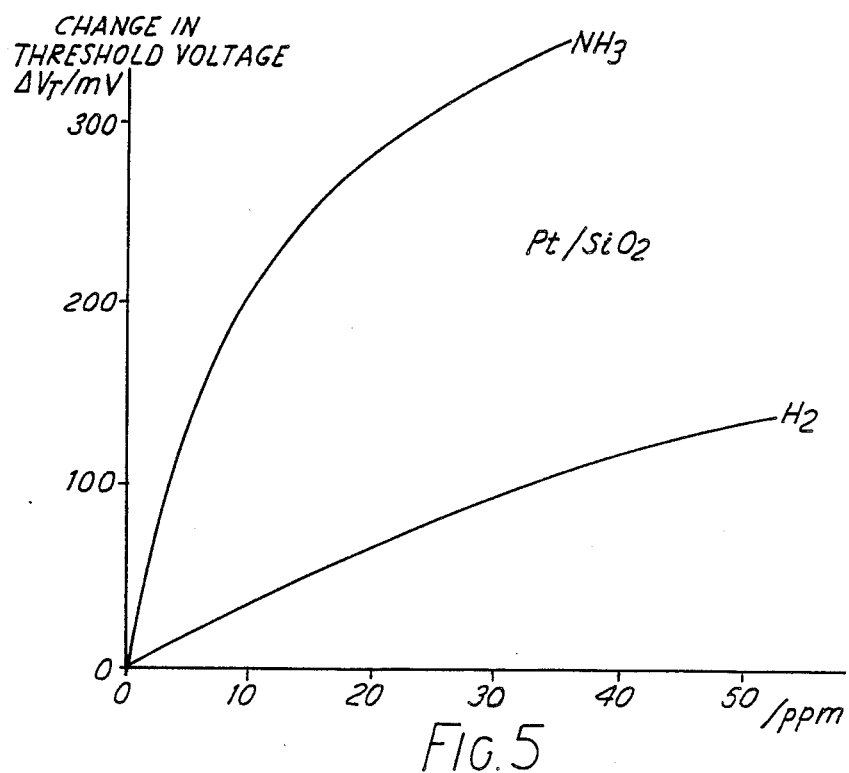
Figure 6:
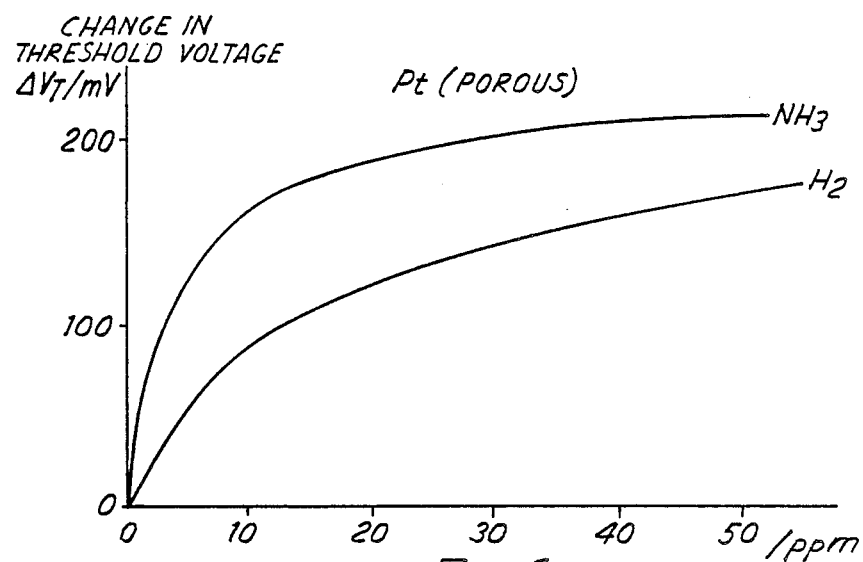

By way of illustration, FIG. 4 demonstrates how two gas sensitive MISFETs, provided with different gate electrode structures respond to methane. Curve A in FIG. 4 shows the response of a MISFET, in accordance with the present invention, wherein a composite gate electrode comprises an intimate mixture of platinum and silicon dioxide in the mass ratio 10:1, and curve B shows the response of a known MISFET, wherein the gate electrode comprises a thin porous film of pure platinum, deposited by evaporation. It will be apparent that a MISFET in accordance with the present invention, wherein the gate electrode has a composite structure, has a markedly enhanced sensitivity to methane. Similarly FIGS. 5 and 6 show how the two MISFETs respond to ammonia gas and to hydrogen. Again it will be apparent that a MISFET with a composite gate electrode has a greater sensitivity to ammonia gas, and, moreover, exhibits greater selectivity of ammonia gas as compared with hydrogen. A MISFET having a non-porous platinum gate is found to be relatively insensitive to both ammonia gas and methane.

Figure 7:
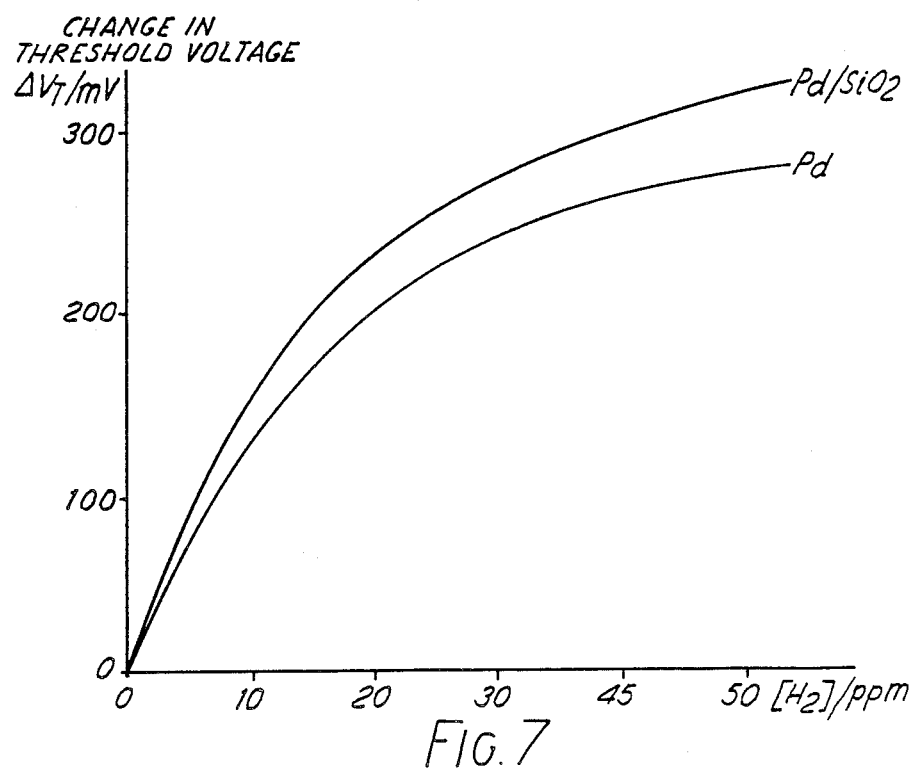
Figure 8:
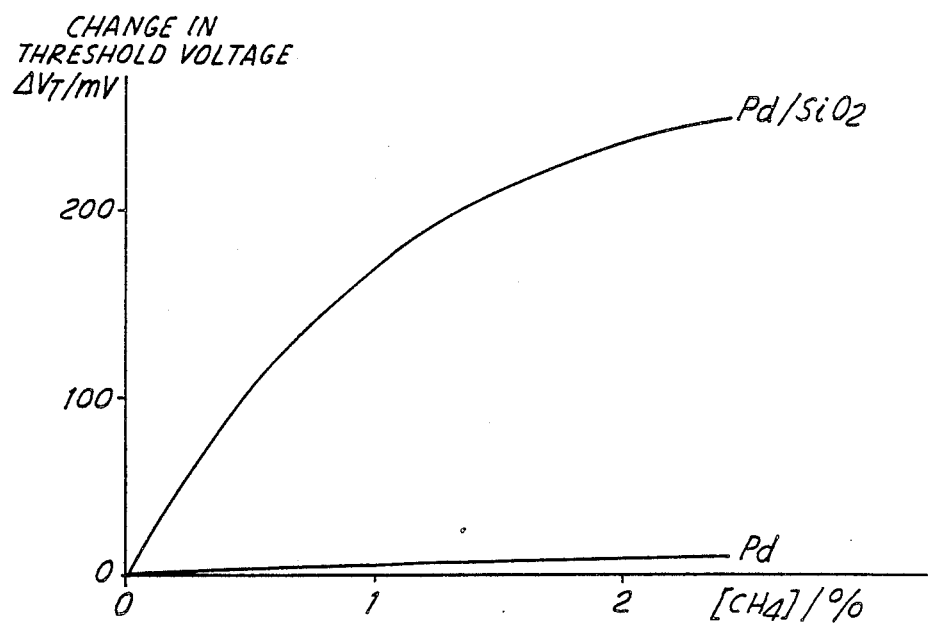

Similarly, it will be apparent from FIGS. 7 and 8 that a MISFET wherein the gate electrode comprises an intimate mixture of palladium and silicon dioxide (in the mass ratio 10:1) has a greater sensitivity to methane than does a MISFET wherein the gate electrode is comprised solely of palladium, and exhibits a greater selectivity of methane as compared with hydrogen.

In another application of the present invention a composite material comprising a catalytically active metal and a non-metallic material, as described hereinbefore by reference to FIGS. 1 to 6 of the accompanying drawings, is applied, as a coating, to an optical fibre constituting the gas-sensitive element of an optical fibre gas sensor.

In an example, the coating comprises an intimate mixture of palladium (or platinum) and silicon dioxide deposited on the optical fibre by a co-sputtering technique to form a cermet. This may be achieved either by sputtering the constituent materials simultaneously or, alternatively, by presenting the constituent materials alternately for short, predetermined intervals of time. In operation of the sensor, hydrogen gas, or a hydrogen-containing gas (e.g. $CH_4$, $H_2S$, $NH_3$), to which the coating is exposed undergoes a catalytic reaction and is caused to dissociate. Free hydrogen is formed which, in this case, reacts with the palladium (or platinum) to form a hydride $PdH_x$ (or $PtH_x$). The lattice constant increases with the value of x, causing strain in the fibre. In other cases, strain arising from an exothermic or endothermic reaction may dominate, or both effects may be significant. The resulting strain is then detected optically by monitoring interference of laser light emergent from both a coated fibre and an uncoated, reference fibre. An article entitled "Optical fibre hydrogen sensor" Appl. Phys Letters 45 (10) 15 Nov. 1984 p1007 and 1008 describes a suitable interferometer arrangement.

The inventors envisage that, as compared with a composite gate electrode of the kind described hereinbefore, an optical fibre coated with a composite material gives rise to greater catalytic activity and enhanced selectivity with respect to certain hydrogen containing gases, notably $CH_4$ and $NH_3$.

In an alternative embodiment the coating could comprise a layer comprised solely of a catalytically active metal (e.g. Pt or Pd) provided with a further layer comprising an intimate mixture of a catalytically active metal and a non-metallic material (eg Pt or Pd and $SiO_2$). In a yet further embodiment the coating may comprise a layer comprised solely of a catalytically active metal provided with a coating of a non-metallic material eg $SiO_2$.

An optical fibre gas sensor of the kind described may comprise one or more coated fibres of desired length and provides a very effective form of distributed sensor.

It will be understood that a device in accordance with the present invention is not limited to use of a gas sensitive element (e.g. an electrode or coating) containing platinum or palladium. Other catalytically active metals could be used, notably metals selected from the Group VIII transition metals i.e palladium, platinum, rhodium, ruthenium, iridium, osmium, cobalt and nickel and alloys thereof.

Similarly, the gas sensitive element could contain a non-metallic material other than silicon dioxide, for example materials useful as support media for catalysts eg aluminium oxide, titanium dioxide, cerium dioxide, magnesium oxide, vanadium pentoxide, metal zeolites, and mixtures formed from two or more of these materials.

The inventors have found that a composite gate electrode in accordance with the invention can be manufactured with relative reliability-yields as high as 80% have been achieved. In comparison, it is found that manufacture of a thin, porous electrode of pure platinum, suitable for use in a MISFET, is much less reliable due to the severe constraints which must be imposed on thickness, porosity etc in order to achieve satisfactory operation.

We claim:

1. A gas-sensitive field effect device includes a gas-sensitive gate electrode comprising a catalytically active metal and a non-metallic material mixed with, or deposited at an exposed surface of, the metal wherein said non-metallic material enhances the catalytic activity of the metal and is selected from the group consisting of an oxide of a metal, an oxide of a semiconductor, a metal zeolite and mixtures of more than one of said non-metallic materials the catalytically active metal and the non-metallic material being formed as an intimate mixture, the threshold voltage of the device thus varying dependent on the quantity of a gas incident on the gate electrode.

2. A gas-sensitive device according to claim 1 wherein said electrode comprises a first layer of a first catalytically active metal bearing a second layer of a second catalytically active metal mixed with said non-metallic material.

3. A gas sensitive field effect device according to claim 2, wherein said first and second layers contain the same catalytically active metal.

4. A gas sensitive field effect device according to claim 1, wherein a said catalytically active metal comprises a selected one of, or an alloy formd from two or more of, the transition metals.

5. A gas sensitive field effect device according to claim 1, wherein said non-metallic material comprises a selected one of, or a mixture formed from two or more of, the group consisting of silicon dioxide, aluminium oxide, titanium dioxide, cerium dioxide, magnesium oxide, vanadium pentoxide, and metal zeolites.

6. A gas sensitive field effect device according to claim 1, wherein said gas sensitive electrode includes a mixture of platinum or palladium and silicon dioxide.

7. A gas sensitive field effect device according to claim 1, wherein said gas sensitive element is deposited by co-sputtering the constituents.

8. An optical fibre gas sensor comprising an optical fibre and a gas-sensitive coating deposited at a surface of the optical fibre, wherein said coating comprises a catalytically active metal and a non-metallic material mixed with, or deposited at an exposed surface of, the metal, and said non-metallic material modifies the catalytic activity of the metal and is selected from the group consisting of an oxide of a metal, an oxide of a semiconductor, a metal zeolite and mixtures of more than one of said non-metallic materials.

9. A gas sensor according to claim 8 wherein said gas sensitive coating includes a mixture of platinum or palladium and silicon dioxide.

10. A gas sensor according to claim 9 wherein said gas sensitive element is deposited by co-sputtering the constituents.

11. A gas-sensitive device according to claim 1 in which the ratio of the mass of catalytically active metal to the non-metallic mixture is at least 10:1.

* * * * *